US011266844B2

(12) United States Patent
von Huben

(10) Patent No.: US 11,266,844 B2
(45) Date of Patent: Mar. 8, 2022

(54) FEEDTHROUGH ARRANGEMENT FOR MEDICAL DEVICE

(71) Applicant: Cochlear Limited, Macquarie University (AU)

(72) Inventor: Mark Alan von Huben, Macquarie University (AU)

(73) Assignee: Cochlear Limited, Macquire University (AU)

( * ) Notice: Subject to any disclaimer, the term of this patent is extended or adjusted under 35 U.S.C. 154(b) by 227 days.

(21) Appl. No.: 16/741,385

(22) Filed: Jan. 13, 2020

(65) Prior Publication Data
US 2020/0147399 A1    May 14, 2020

Related U.S. Application Data

(62) Division of application No. 15/416,154, filed on Jan. 26, 2017, now Pat. No. 10,556,115.

(60) Provisional application No. 62/289,116, filed on Jan. 29, 2016.

(51) Int. Cl.
*A61N 1/375* (2006.01)
*A61N 1/36* (2006.01)
*A61N 1/05* (2006.01)

(52) U.S. Cl.
CPC .......... *A61N 1/3754* (2013.01); *A61N 1/0541* (2013.01); *A61N 1/36038* (2017.08)

(58) Field of Classification Search
CPC . A61N 1/3754; A61N 1/36038; A61N 1/0541
See application file for complete search history.

(56) References Cited

U.S. PATENT DOCUMENTS

| 8,515,540 | B2 | 8/2013 | Leigh et al. |
| 10,556,115 | B2 | 2/2020 | von Huben |
| 2005/0007718 | A1 | 1/2005 | Stevenson et al. |
| 2009/0123810 | A1 | 5/2009 | Devoe et al. |
| 2011/0059331 | A1 | 3/2011 | Smith et al. |
| 2014/0163626 | A1 | 6/2014 | Walling et al. |

*Primary Examiner* — Catherine M Voorhees
*Assistant Examiner* — Roland Dinga
(74) *Attorney, Agent, or Firm* — Edell, Shapiro & Finnan, LLC

(57) ABSTRACT

A feedthrough for a cochlear implant or other medical device can include contacts disposed on an outer perimeter thereof. By disposing the contacts on the perimeter, the number of contacts on the feedthrough can be increased, the size of the feedthrough reduced, or both.

20 Claims, 7 Drawing Sheets

FEEDTHROUGH ARRANGEMENT FOR MEDICAL DEVICE

CROSS REFERENCE TO RELATED APPLICATION

This application is a divisional of U.S. application Ser. No. 15/416,154 filed Jan. 26, 2017, which claims priority to U.S. Application No. 62/289,116, titled FEEDTHROUGH ARRANGEMENT FOR MEDICAL DEVICE, filed on Jan. 29, 2016, the disclosure of which are hereby incorporated by reference in their entirety.

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a recipient experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

It can be desirable that feedthroughs for medical devices, such as, cochlear implants are small. However, the feedthrough vias need to be a minimum size to allow reliable joining. A minimum spacing between vias is also required to stop electrical leakage therebetween. Historically, vias have been placed on the planar surfaces of feedthroughs. However, it has been discovered that vias can also be disposed on non-planar surface, such as the outer perimeter of a cylindrical feedthrough. In doing so, the size of the feedthrough can be reduced, the number of vias increased, and/or better contact with output wires can be achieved.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The technologies disclosed herein can be used in conjunction with various types of implantable electronics. For clarity, however, the technology will be described in the context of an auditory prosthesis such as a cochlear implant that utilizes both an external portion and an implantable portion. Of course, one of skill in the art will appreciate that the feedthrough configurations described here can also be utilized with totally implantable cochlear implants as well, or with other medical devices that require a significant number of electrical connections at a very small overall size. Such medical devices include, but are not limited to retinal implants, or other small-scale medical devices.

Figure 1:
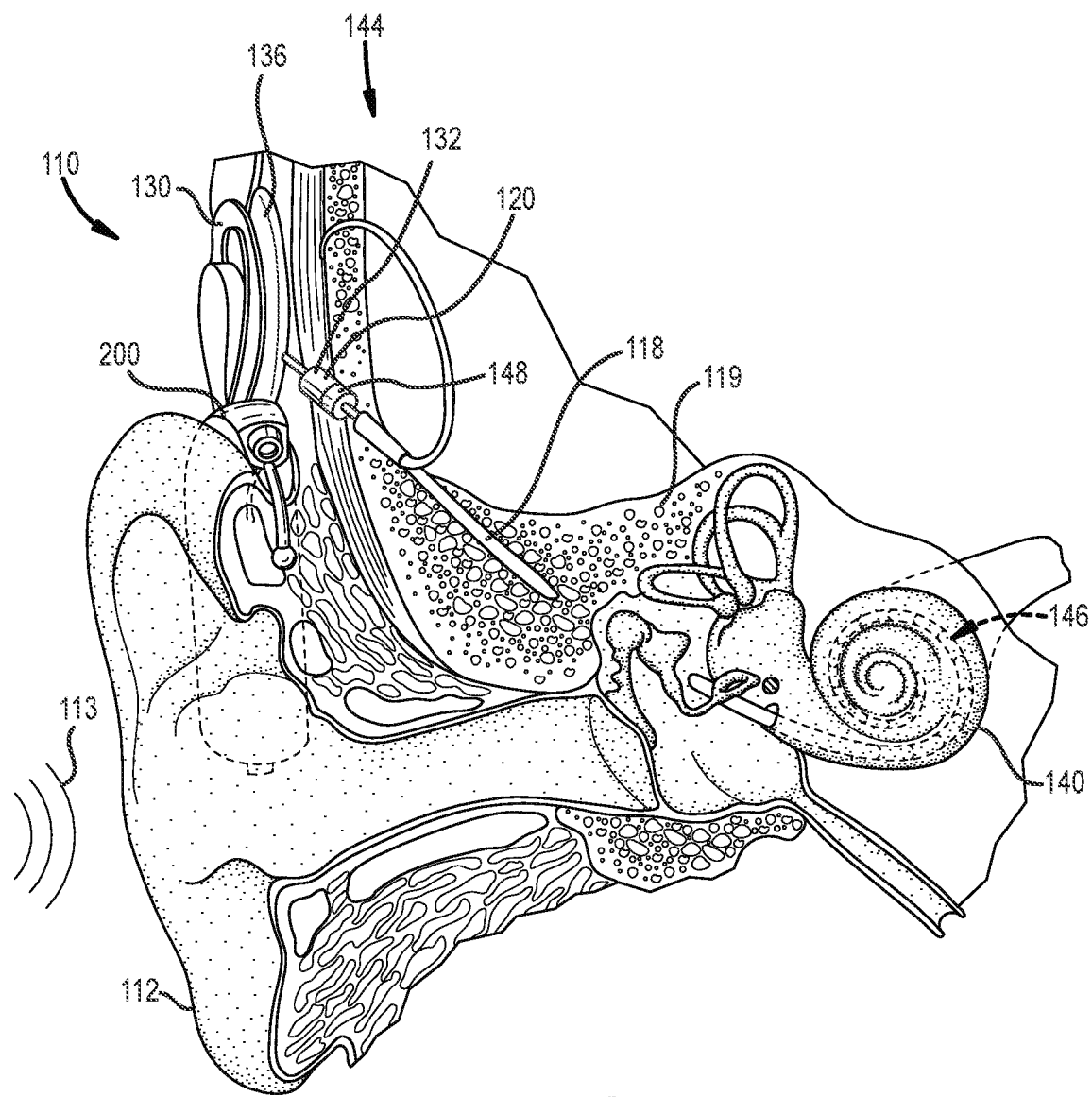
FIG. 1 is a partial view of a behind-the-ear auditory prosthesis worn on a recipient.

Referring to FIG. 1, cochlear implant system 110 includes an implantable component 144 typically having an internal receiver/transceiver and stimulator unit 132 disposed in a chassis 120, and an elongate lead 118. The internal receiver/transceiver unit 132 permits the cochlear implant system 110 to receive and/or transmit signals to an external device. The external device can be a button sound processor worn on the head that includes a receiver/transceiver coil and sound processing components. Alternatively, the external device can be just a receiver/transceiver coil in communication with a BTE device 200 that includes the sound processing components and microphone. The implantable component 144 includes an internal coil 136, and preferably, a magnet (not shown) fixed relative to the internal coil 136. Signals sent generally correspond to external sound 113. The internal receiver/transceiver and stimulator unit 132 is hermetically sealed within a biocompatible chassis 120. The magnets facilitate the operational alignment of the external and internal coils, enabling internal coil 136 to receive power and stimulation data from external coil 130. The external coil 130 is contained within the external device, which is not shown. Elongate lead 118 has a proximal end connected to the chassis 120 at a feedthrough 148, and a distal end implanted in cochlea 140. Elongate lead 118 extends from chassis 120 to cochlea 140 through mastoid bone 119.

The elongate lead 118 is connected to the chassis 120 that contains the electronics required to process the signals sent from the external coil 130 into signals that are sent to the recipient. The implant chassis 120 can be in any configuration as required or desired for a particular application and is sealed to a feedthrough 148 so as to form a hermetically sealed chamber. The feedthrough 148 includes a number of discrete vias, as described in more detail below, that are arranged on one or more surfaces thereof. The feedthrough 148 provides numerous electronic points of connection between the wires in the elongate lead 118 and the electronics contained within the chassis 120. As such, it can be desirable to arrange a significant number of vias on the feedthrough, while keeping the total feedthrough size as small as possible. In fact, although the chassis is depicted as being proximate the internal coil 136, the chassis 120 can be located a considerable distance from the coil 136, e.g., closer to the intra-cochlear assembly 146. In examples, the chassis 120 can be disposed within the mastoid bone 119 so as to provide protection to the chassis 120 and feedthrough 148.

In certain examples, external coil 130 transmits electrical signals (e.g., power and stimulation data) to internal coil 136 via a radio frequency (RF) link, as noted above. Internal coil 136 is typically a wire antenna coil comprised of multiple turns of electrically insulated single-strand or multi-strand platinum or gold wire. The electrical insulation of internal coil 136 is provided by a flexible silicone molding. In use, implantable receiver unit 132 is conventionally positioned in a recess of the temporal bone adjacent auricle 110 of the recipient. However, the technologies disclosed herein can facilitate alternate implant placements, such as within a cavity in the mastoid bone or within the middle ear cavity, through efficient use of space within the hermetic enclosure. Various types of energy transfer, such as infrared (IR), electromagnetic, capacitive and inductive transfer, can be used to transfer the power and/or data from external device to cochlear implant.

Figure 2:
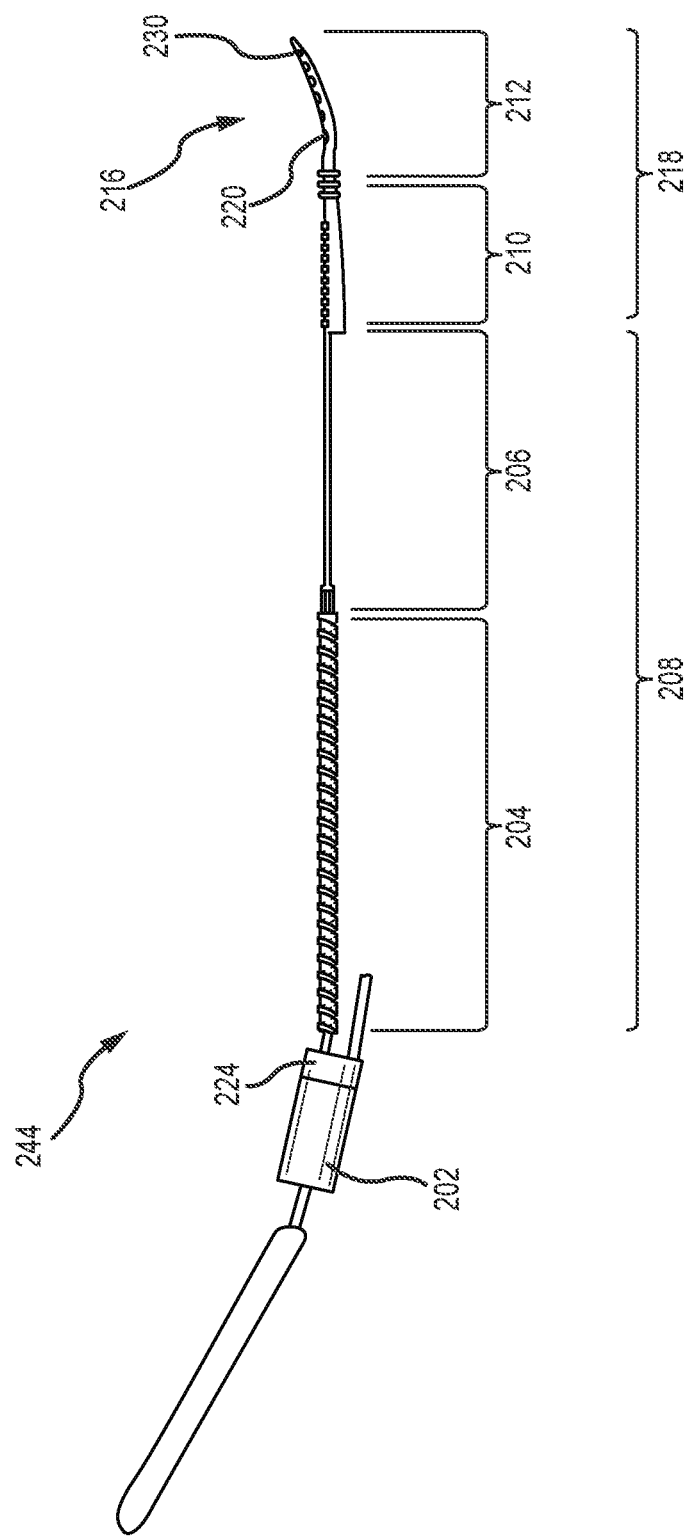
FIG. 2 is a side view of an example of an implantable portion of an auditory prosthesis.

FIG. 2 is a simplified side view of an internal component 244 having a stimulator/receiver unit encased within a chassis 202. The stimulator/receiver unit receives encoded signals from an external component of the cochlear implant system, processes those signal, and sends stimuli to the recipient. Internal component 244 terminates in a stimulating assembly 218 that comprises an extra-cochlear region 210 and an intra-cochlear region 212. Intra-cochlear region 212 is configured to be implanted in the recipient's cochlea and has disposed thereon a contact array 216. In the present example, contact array 216 can be electrical stimulation contacts 230.

Internal component 244 further comprises a lead region 208 coupling chassis 202 to stimulating assembly 218, via a number of vias on a feedthrough 224. The feedthough 224 seals the chassis 202 so as to form a hermetically-sealed enclosure. The feedthrough 224 includes a number of vias (not shown) that are used to electrically connect wires in the lead region 208 to the electronics within the chassis 202, so as to allow transmission of signals from the stimulator/receiver unit to the electrical contacts 230 in the cochlea. Lead region 208 comprises a region 204 which is commonly referred to as a helix region, however, the required property is that the lead accommodate movement and is flexible, it does not need to be formed from wire wound helically.

Reduction in size of implanted medical devices can produce a number of benefits. At a minimum, a smaller medical device can cause a commensurate decrease the size of an implantation site. This limits the amount of trauma to tissue during implantation and allows certain devices to be less noticeable when worn by a recipient. A number of configurations of feedthroughs that can be used in medical devices are described below.

In some of the following configurations, the feedthrough vias terminate at contact pads that are disposed on the non-hermetic side of the feedthrough. The contact pads are conductive surfaces that facilitate electrical connection with the implant electronics disposed within the hermetic enclosure through the vias. A compatible implant component (such as lead 118 shown in FIG. 1) electrically connects to the implant electronics by making physical contact with pads. This can be facilitated via a reciprocal female connector part that envelops the feedthrough. The contacts are depicted disposed on various surfaces of a feedthrough, for clarity. In other examples, depending on the thickness of the feedthrough, the contacts can also be recessed within the surfaces of the feedthrough, with no loss of performance. The feedthrough can be joined to an associated chassis with braze joints, chemical adhesives, or other joining systems as known in the art, so as to hermetically seal the electronics into a closed housing defined by the feedthrough and the chassis. By disposing contacts in or on non-planar surfaces of a feedthrough, the total surface area available for contacts can be significantly increased.

The technologies described herein relate generally to feedthrough having vias disposed on perimeter surfaces thereof, as opposed to or in addition to disposition on an end surface of the feedthrough. Perimeter surfaces can generally be perimeters of a feedthrough body that are substantially cylindrically shaped, and have a circular outer perimeter. Other outer perimeter form factors are contemplated, and include oval, squircle, rounded rectangle, rounded square, and so on. In an example, a perimeter surface of a feedthrough can be described as a substantially continuous outer surface that extends about most of the feedthrough body. The perimeter surface of the feedthrough can also form an outer surface of the implant housing, formed by the feedthough and the chassis. Where the feedthrough forms part of a connector, the perimeter surface of the feedthrough typically coincides with the perimeter, or a localized perimeter, of the implant housing.

In examples, the perimeter may extend about more than one-half of the feedthrough body and up to about 360° of the body. In examples, this perimeter surface is unbroken by sharp angular transitions. By utilizing an exposed perimeter surface of a feedthrough for the disposition of vias, a number of advantages are apparent. One advantage is that a significantly larger surface area can be available for the placement of contacts, as compared to a feedthrough that disposes vias only on a single, exposed end surface thereof. This would allow for a higher number of vias/contacts to be utilized on the feedthrough. Another advantage is that the larger available surface area can be used to place an equal number of contacts on a feedthrough, while reducing the overall size of the feedthrough by distributing the contacts on both an end surface and a perimeter surface of the feedthrough. Other advantages are described throughout the specification and further advantages will be apparent to a person of skill in the art. The vias/contacts described herein can be used for both incoming and outgoing signals.

Figure 3A:
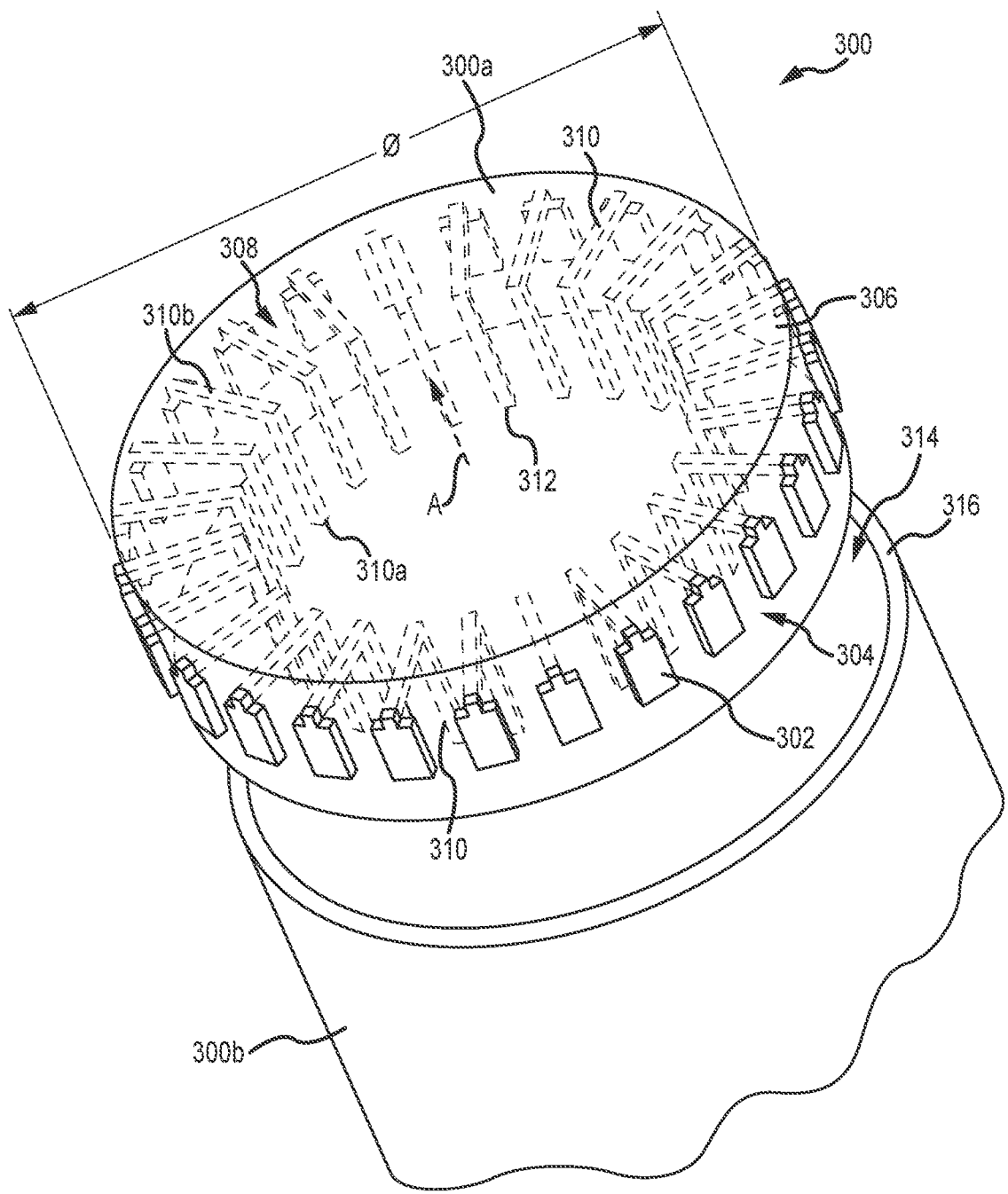
FIG. 3A is an exploded perspective view of a medical device implant body.
Figure 3B:
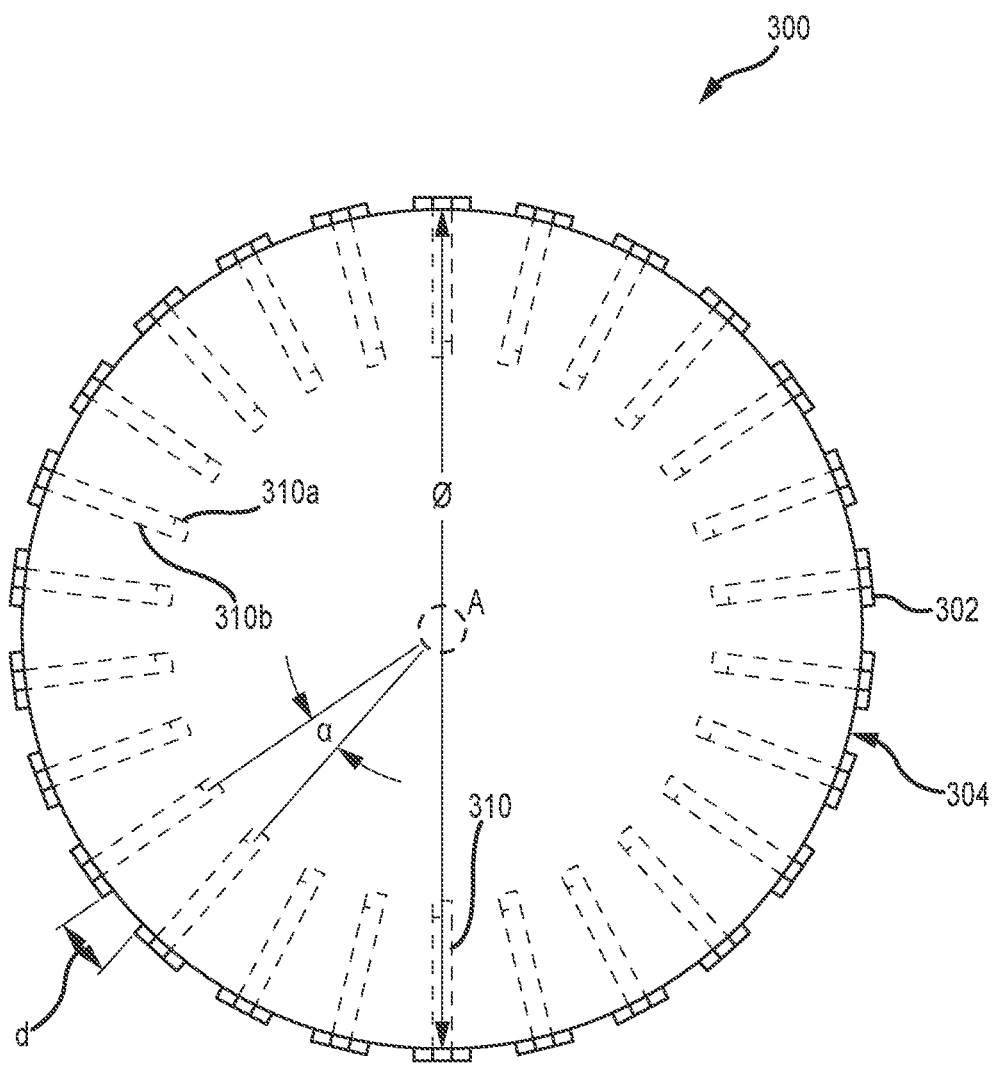
FIG. 3B is plan view of an example of a feedthrough having contacts on an outer perimeter surface thereof.

FIG. 3A is an exploded perspective view of a medical device implant body 300 comprising a structural chassis 300b and an electrical feedthrough 300a. FIG. 3B is plan view of the implant body 300 showing the feedthrough 300a. FIGS. 3A and 3B are described simultaneously. The feedthrough 300a includes an insulated body 306, such as ceramic or other non-conductive material (e.g., plastic) that includes both two end planar outer surfaces 308 and a single perimeter non-planar outer surface 304 disposed approximately 90 degrees thereto. Contacts 302 are disposed on the perimeter surface 304, which here is circumferential, as the feedthrough 300 is substantially round in shape. The perimeter surface 304 of the feedthrough 300a also coincides with the perimeter surface of the chassis 300b in the illustrated embodiment. In other examples, contacts can also be disposed on one or both of the end planar outer surface 308 or a combination of contacts and pins (such as the exposed ends of the vias) can be utilized. Each contact 302 is evenly spaced about the non-planar surface 304 by a distance d, which should be sufficient to minimize or eliminate electrical leakage between adjacent contacts 302. The body 306 defines a central axis A. Each contact 302 is connected to a single via 310 of conductive material. As such, each contact 302 is in electrical communication with a single via 310. Because the contacts 302 depicted in FIGS. 3A and 3B are disposed about the outer non-planar surface 304, each via 310 is particularly configured so as to pass through the body 306 to reach a respective contact 302.

The contacts 302 are depicted as enlarged, substantially two-dimensional pads that are disposed on the outer non-planar surface 304 of the feedthrough 300. While this configuration is particularly desirable for the use in conjunction with the sleeve and feedthrough connector of FIGS. 6 and 7, other contact configurations are contemplated.

Figure 5:
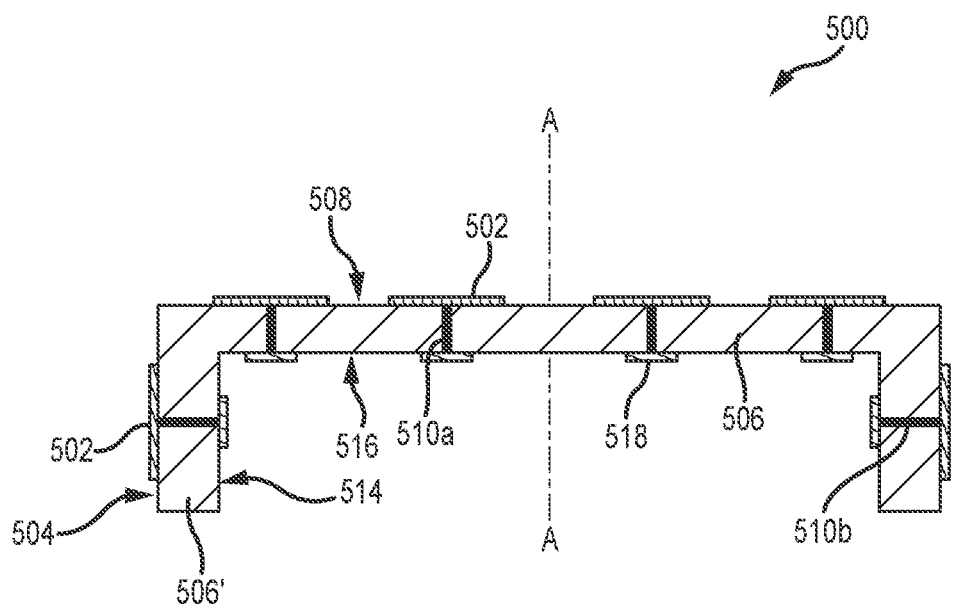
FIG. 5 is a side sectional view of an example of a feedthrough having contacts on outer non-planar perimeter surface and an outer planar end surface thereof.

In the depicted example, each via 310 includes a parallel portion 310a and a diverging portion 310b. Each parallel portion 310a is substantially parallel to the axis A of the body 306. As such, the parallel portion 310a of one via 310 is substantially parallel to the other parallel portions 310a of the other vias 310. Each diverging portion 310b diverges away from an adjacent diverging portion 310b as the via 310 extends away from the axis A. As such, each diverging portion 310b is substantially orthogonal to the non-planar perimeter surface where that diverging portion 310b contacts its associated contact 302. Both parallel portion 310a and diverging portion 310b can be embedded in the non-conductive body of the feedthrough. Alternatively, the feedthrough can have a profile that facilitates access to an inner perimeter surface as depicted in FIG. 5.

An angle α can be measured between each diverging portion 310b and can vary depending on the number, size, and/or position of the contacts 302 about the perimeter surface 304. In the twenty-six contact configuration of FIGS. 3A and 3B, the angle α is about 14°. Other angles α are contemplated. Additionally, in this configuration, if utilizing contacts 302 about 0.3 mm wide with 0.3 mm spacing between adjacent contacts 302, the diameter ϕ of the body 306 is about 5.0 mm. If the contact size and spacing of 0.3 mm is maintained, but only twenty-two contacts 302 utilized, the diameter ϕ can be reduced to about 4.22 mm. Of course, greater or lesser number of contacts can be utilized. Since the vias 310 include both parallel 310a and diverging 310b portions, the entire length of the via (from a termination point 312 to the associated contact 302) can be described as non-linear along its entire length (since the via 310 is not a straight line between two surfaces of the body 306). Other arrangements of vias are contemplated and described in U.S. Pat. No. 8,515,540, the disclosure of which is hereby incorporated by reference herein in its entirety. Moreover, the contacts 302 need not be evenly dispersed about the entire perimeter, but can be spaced as required or desired for a particular application. The feedthrough 300a can be secured to a chassis 300b in which is disposed the electronics required to process and deliver signals to a recipient of the medical device implant body 300. The medical device implant body 300 may form a portion of a larger medical device and is configured to support and protect electronics that are disposed therein.

In the depicted configuration, the electronics chassis 300b is configured as a substantially cylindrically shaped body having an open end 314. The open end 314 can be defined by a perimeter contact surface 316 to which the feedthrough 300a can be secured via brazing, adhesives, welding, or other securement elements or techniques. Once secured, the feedthrough 300a and the chassis 300b form a hermetically-sealed unit that protects the electronics from damage, infiltration by bodily fluids, and so on. The materials utilized in the implant bodies described herein can be those typically used for such bodies. For example, the chasses 300b can be formed of metals such as titanium, as well as ceramics and robust plastics. The feedthroughs 300a (the bodies 306, specifically) can be formed of non-conductive materials such as ceramics and plastics.

Figure 4:
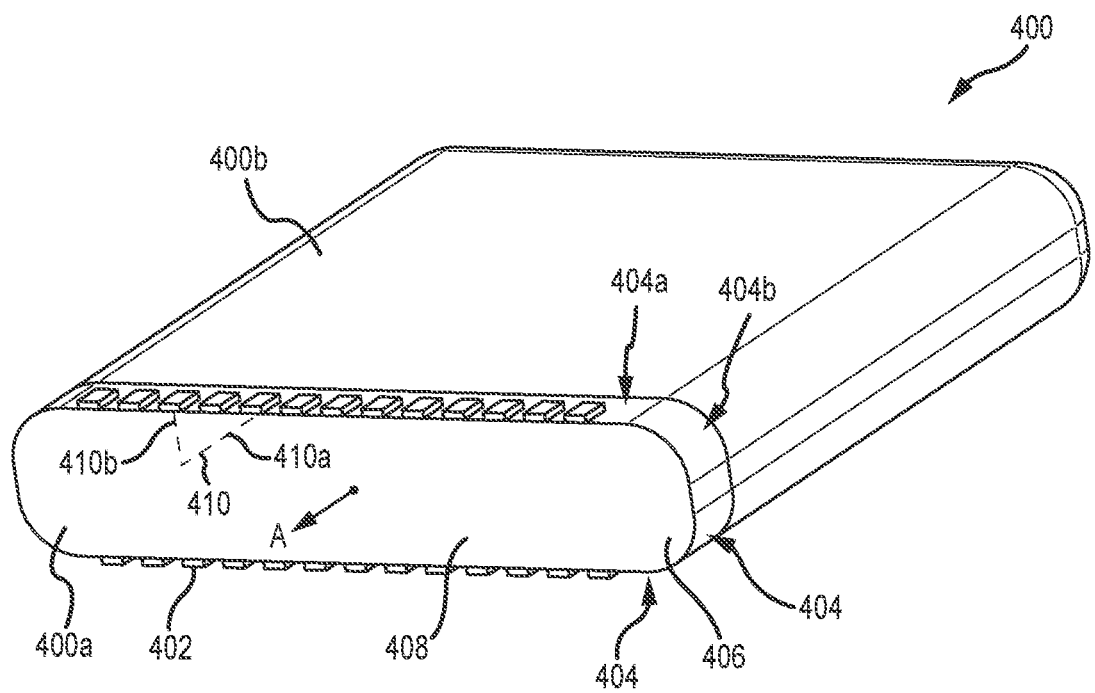
FIG. 4 is a perspective view of an example of an implant housing comprising a chassis and a feedthrough having contacts on an outer perimeter surface thereof.

FIG. 4 is a perspective view of an example of a medical device implant body 400 having a chassis 400b and a feedthrough 400a with contacts 402 on an outer perimeter surface 404 thereof. In the depicted configuration, the outer perimeter surface 404 is a continuous surface having both planar portions 404a and non-planar portions 404b. Contacts 402 can also be disposed on the non-planar portions 404b. A single exemplary via 410 is depicted. The via 410 includes a parallel portion 410a, configured to be parallel to an axis A of the body 406. A second portion 410b is, in this case, not diverging from other, adjacent second portions 410b. This second portion 410b is, however, still orthogonal to the outer perimeter surface 404 of the body 406, and is also substantially parallel to adjacent second portions 410b of vias 410. Of course, contacts 402 disposed along the non-planar surface 404b would have diverging portions of vias, as described above. As above, a planar end surface 408 is disposed substantially orthogonal to both the planar perimeter surface 404a and the non-planar perimeter surface 404b. The via 410 can be connected via wires to electronics disposed within chassis 400b, as described above with regard to FIGS. 3A and 3B. Further, the feedthrough 400a is secured to the chassis 400b so as to form a hermetically-sealed chamber in which the electronics are disposed.

FIG. 5 is a side sectional view of an example of a feedthrough 500 having contacts 502 on outer perimeter surfaces 504 and outer end surfaces 508 thereof. As such, the feedthrough 500 can support a significant number of contacts 502 for use in a medical device such as a cochlear implant. By disposing contacts 502 on both the outer perimeter surface 504 and outer end surface 508, the overall size of the feedthrough 500 can be reduced. The feedthrough 500 is substantially circular in shape and the section of FIG. 5 is depicted proximate a diameter ϕ of the body 506. The body 506 in this case, is substantially dish-shaped, with raised sides 506' that ultimately define an inner non-planar perimeter surface 514 and an inner planar surface 516. Contacts 502 disposed on the outer perimeter surface 504 are in communication with a diverging via portion 510b as defined generally above. Again, diverging via portions 510*b* diverge away from other diverging via portions 510*b* as those vias extend away from an axis A of the feedthrough 500. Contacts 502 disposed on the outer planar surface 508 are in communication with parallel via portions 510*a*. On the inner perimeter surface 514 and the inner planar surface 516, inner contacts 518 can be disposed and in communication with the vias 510*a*, 510*b*. Alternatively, the vias 510*a*, 510*b* can be simply connected to wires, as known in the art.

Figure 6:
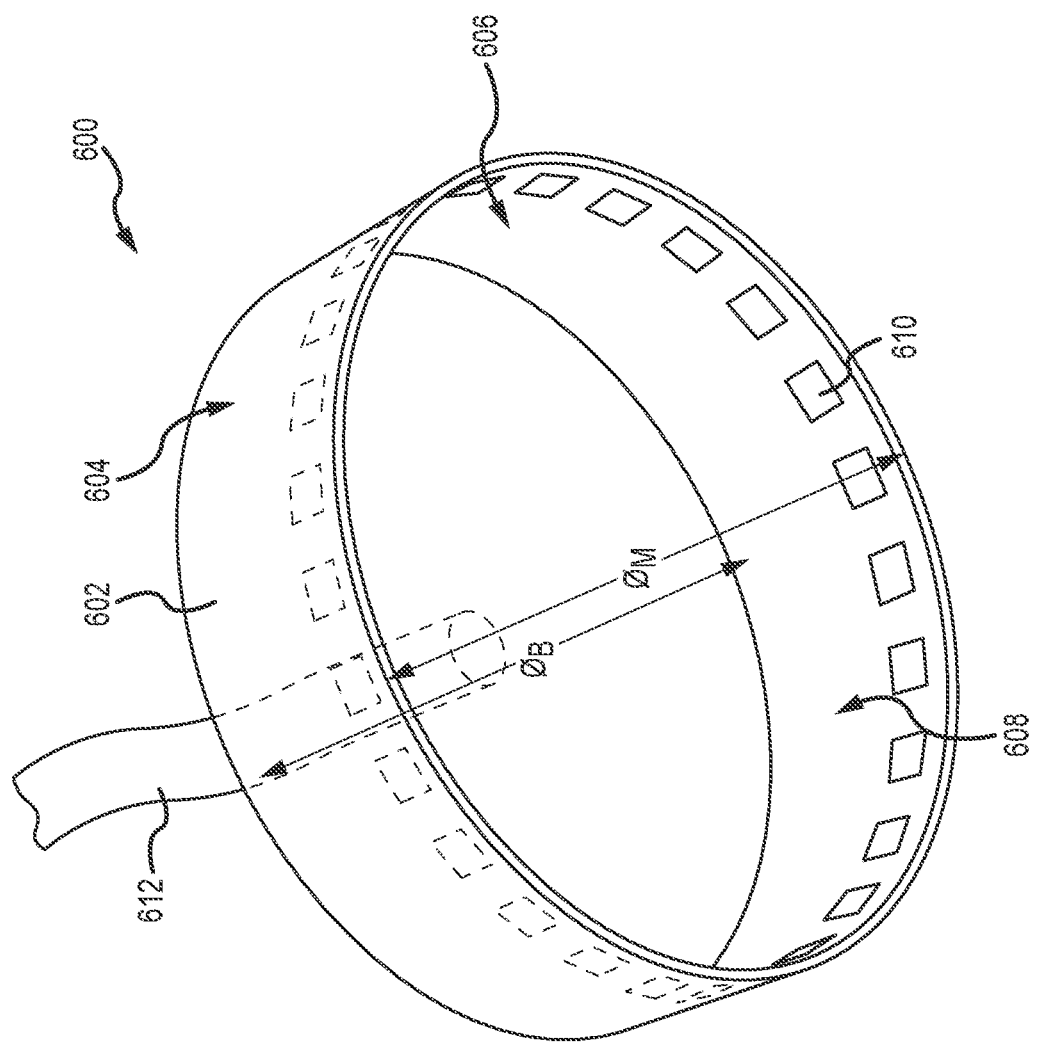
FIG. 6 is a perspective view of an example of a sleeve for receiving a feedthrough.

FIG. 6 is a perspective view of an example of a sleeve 600 for receiving a feedthrough. In the depicted example, the sleeve 600 is substantially annular in shape, although other shapes can be utilized depending on the form factor of the feedthrough. The sleeve 600 can be manufactured having dimensions substantially similar to those of the feedthrough. The sleeve 600 includes an annular body 602 that has an outer surface 604 and an inner surface 606. The inner surface 606 defines a receiver 608 into which a mating feedthrough is inserted. A plurality of contacts 610 are disposed about the inner surface 606 and are connected to the inner surface 606 such that the body 602 can be stretched or otherwise deformed without the contacts 610 being torn therefrom. The number of contacts 610 typically corresponds to the number of contacts on the mating feedthrough. Wires (not shown) from each contact 610 are routed within the body 602 and bundled into a lead 612 in the illustrated example. A diameter $\phi_M$ at a mouth of the receiver 608 can be larger than a diameter $\phi_B$ at a base of the receiver 608. This can cause a higher pressure gradient proximate the base, which can force fluids out of the receiver 608.

The sleeve 600 can be secured about the feedthrough in a variety of ways, some of which are dependent on the type of connection (permanent or releasable) and the material used for the sleeve 600. For example, the material can be a biocompatible heat shrink polymer that can be heat shrunk over the feedthrough. In another example, the sleeve can be heated so as to expand (due to the coefficient of thermal expansion), placed over the feedthrough, and allowed to cool and shrink. If the material is silicone, the silicone can be overmolded and allowed to shrink during curing. In another example, a silicone sleeve can be expanded through the use of chemicals like Lenium or nHeptane and placed over the feedthrough. As the chemical evaporates, the silicone sleeve will shrink about the feedthrough. In another example, a tape, suture or wire can be wound around the feedthrough and sleeve under tension, typically during surgery. For non-releasable connections, the sleeve can be crimped or similarly secured to the feedthrough during production. In examples, the sleeve contacts surface portions of the feedthrough between the contacts, so as to form an adequate seal between adjacent contacts.

Figure 7:
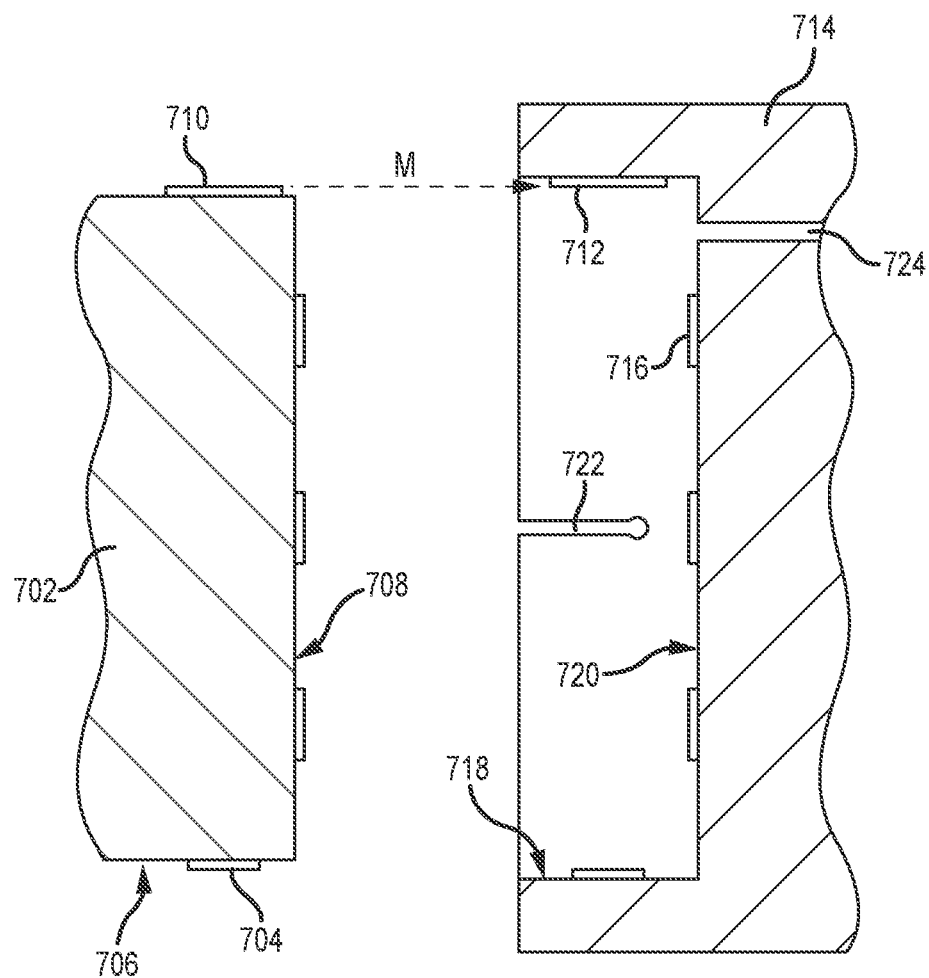
FIG. 7 is a side sectional view of an example of a feedthrough connector.

FIG. 7 is a side sectional view of an example of a feedthrough connector system 700, depicting another example of a configuration to apply even forces about a feedthrough 702. The feedthrough 702 is ceramic and includes a number of contacts 704 on both perimeter surfaces 706 and end surfaces 708. Additionally, the feedthrough 702 includes a key structure 710 that is configured to slidably mate M with a slot 712 on the sleeve 714. The key 710 and slot 712 can help ensure that the feedthrough 702 is only installed in a single orientation. In this case, the sleeve 714 is formed as a split metal tube-like structure, out of a material such as titanium. A number of contacts 716 are disposed on inner perimeter surfaces 718 and inner end surfaces 720. With one or more splits 722 in the sleeve 714, the sleeve 714 can be placed about the feedthrough 702. The split 722 can then be laser welded. As the weld cools, it shrinks so as to provide even force about the feedthrough 702. The sleeve 714 can also include a drain channel 724 through which liquid such as saline or body fluids can be forced from the sleeve 714 during insertion of the feedthrough 702. This can be advantageous if the connection is made during surgical procedures and can be incorporated into the other sleeve examples described herein. Either of the sleeve 714 or feedthrough 702 can include an o-ring, washer, or other sealing element to help ensure an adequate seal.

In general, the feedthroughs depicted in FIGS. 3A-5 are in a male configuration, with contacts disposed along outer surfaces thereof. Placing the contacts about an outer perimeter surface of a feedthrough allows radial pressure to be evenly applied to the contacts, when sleeves such as those depicted as sleeve 600 (FIG. 6) and sleeve 714 (FIG. 7) are utilized in conjunction with the male feedthroughs. An advantage of radial pressure on ceramic feedthrough material is that the pressure is very even and unlikely to cause damage to the feedthrough, since ceramics are strong in compression. Radial pressure can be applied, in one example, with a female, annular sleeve, e.g., as depicted in FIGS. 6 and 7. Radial pressure can be used to form an electrical connection between an electrode wire and the feedthrough without creating a joint (as typically created by crimping or welding). Other systems and configurations for applying radial pressure are contemplated.

The sleeve configuration of FIGS. 6 and 7 display a number of other advantages. For example, this configuration can make implantation of a medical device utilizing such a feedthrough/sleeve connection significantly easier. For example, a surgeon can first implant an electrode (e.g., for an auditory prosthesis) within the recipient. The electrode can include, at a proximate end, a sleeve such as those depicted herein. This can make manipulation of the electrode easier and increase visibility thereof during implantation. Thereafter, the surgeon can implant the portion of the auditory prosthesis having an exposed feedthrough. Once both components are implanted, the sleeve can be connected to the feedthrough.

In another example, an already-implanted stimulator body can be disconnected and replaced with a new stimulator body (e.g., due to failure or stimulator upgrade). This allows for disassembly without necessarily damaging other parts of the implant. Additionally, during manufacture, a production line can have stocks of stimulator bodies and various electrodes on hand. This would allow custom-configured implants to be made to order. It also allows subsequent manufacturing steps after assembly to ensure reliable sealing or electrical connections.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. An apparatus comprising:
a hermetically sealed biocompatible housing having a feedthrough with a plurality of vias that terminate in electrical contacts disposed adjacent an outer surface of the biocompatible housing; and
a flexible sleeve configured to be disposed about the feedthrough, wherein the flexible sleeve defines an inner surface and a plurality of reciprocal electrical contacts disposed on the inner surface,
wherein each of the plurality of reciprocal electrical contacts on the flexible sleeve are disposed so as to form an electrical connection with the electrical contacts on the feedthrough when the flexible sleeve is disposed about the feedthrough.

2. The apparatus of claim 1, wherein the feedthrough forms a perimeter surface of the biocompatible housing and the flexible sleeve is sized so as to apply a compressive force substantially uniformly about the perimeter surface.

3. The apparatus of claim 1, wherein the electrical contacts of the biocompatible housing are recessed in the feedthrough adjacent the outer surface.

4. The apparatus of claim 3, wherein:
the plurality of reciprocal electrical contacts on the flexible sleeve protrudes from the inner surface to positively engage with the electrical contacts recessed in the feedthrough; and
the flexible sleeve has a deformable seal formed around each of the plurality of reciprocal electrical contacts.

5. The apparatus of claim 1, wherein when the flexible sleeve is disposed about the feedthrough, the inner surface of the flexible sleeve touches the outer surface.

6. The apparatus of claim 1, further comprising an electrical stimulation lead bundling a plurality of wires, each respective wire being connected to a respective reciprocal electrical contact of the plurality of reciprocal electrical contacts.

7. The apparatus of claim 1, wherein at least one of the electrical contacts of the biocompatible housing is disposed on a rounded portion of the outer surface of the biocompatible housing.

8. An apparatus comprising:
a sleeve having an inner surface defining a receiver for a mating feedthrough;
a plurality of sleeve contacts disposed at the inner surface;
a lead bundling a plurality of wires, each respective wire being connected to a respective contact of the plurality of sleeve contacts; and
a plurality of electrical stimulation contacts disposed on the lead.

9. The apparatus of claim 8,
wherein the sleeve is flexible, and
wherein each respective contact of the plurality of sleeve contacts is connected to the inner surface in a manner that resists tearing the respective contact when the sleeve is deformed.

10. The apparatus of claim 8,
wherein the receiver defines a mouth having a mouth diameter and a base having a base diameter, and
wherein the mouth diameter is greater than the base diameter.

11. The apparatus of claim 8, wherein the lead comprises an intra-cochlear region and an extra-cochlear region.

12. The apparatus of claim 8, further comprising the mating feedthrough received within the receiver, wherein the mating feedthrough comprises a plurality of feedthrough contacts, each forming a respective electrical connection with a respective sleeve contact of the plurality of sleeve contacts.

13. The apparatus of claim 12,
wherein the sleeve comprises a slot,
wherein the mating feedthrough comprises a key, and
wherein the key and the slot are configured provide an installation orientation between the mating feedthrough and the sleeve.

14. The apparatus of claim 12,
wherein the mating feedthrough comprises a perimeter surface and an end surface,
wherein at least one of the plurality of feedthrough contacts is disposed on the perimeter surface, and
wherein at least one of the plurality of feedthrough contacts is disposed on the end surface.

15. The apparatus of claim 8,
wherein the sleeve is formed as a metal structure, and
wherein the sleeve defines one or more splits in the metal structure.

16. The apparatus of claim 8,
wherein the sleeve defines a drain channel configured to drain fluids during insertion of a feedthrough into the receiver.

17. A method comprising:
securing a sleeve about a mating feedthrough such that a plurality of feedthrough contacts of the mating feedthrough each form a respective electrical connection with a respective sleeve contact of a plurality of sleeve contacts of the sleeve using radial pressure provided by the sleeve.

18. The method of claim 17, wherein securing the sleeve about the mating feedthrough includes shrinking the sleeve about the mating feedthrough by allowing the sleeve to cool or allowing a chemical applied to the sleeve to evaporate.

19. The method of claim 17, further comprising:
implanting an electrode having the sleeve at a proximal end; and
implanting a medical device having the mating feedthrough,
wherein the securing is performed after one or both of the electrode and the medical device are implanted.

20. The method of claim 19,
wherein the securing includes winding a tape, suture, or wire about the sleeve under tension.

* * * * *